(12) United States Patent  
Ahmed (10) Patent No.: US 6,261,256 B1  
(45) Date of Patent: Jul. 17, 2001

(54) POCKET MEDICAL VALVE & METHOD

(76) Inventor: Abdul Mateen Ahmed, 928 E. Juanita Ave., La Verne, CA (US) 91750

( * ) Notice: Subject to any disclaimer, the term of this patent is extended or adjusted under 35 U.S.C. 154(b) by 0 days.

(21) Appl. No.: 08/943,453

(22) Filed: Oct. 3, 1997

Related U.S. Application Data (63) Continuation-in-part of application No. 08/771,446, filed on Dec. 20, 1996, now Pat. No. 5,785,674.

(51) Int. Cl.[7] ..................................... A61M 5/00
(52) U.S. Cl. ..................................... 604/9; 604/8
(58) Field of Search ................. 604/8–10, 289, 604/294, 4; 623/4, 4.1

(56) References Cited

U.S. PATENT DOCUMENTS

| | | |
|---|---|---|
| 4,457,757 | 7/1984 | Molteno . |
| 4,521,210 * | 6/1985 | Wong ........................................ 604/8 |
| 4,554,918 | 11/1985 | White . |
| 4,729,761 * | 3/1988 | White ........................................ 604/8 |
| 5,017,408 | 5/1991 | Kozak . |
| 5,071,408 * | 12/1991 | Ahmed ................................. 606/108 |
| 5,397,300 | 3/1995 | Baerveldt et al. . |
| 5,417,651 | 5/1995 | Guena et al. . |
| 5,433,701 | 7/1995 | Rubenstein . |
| 5,454,796 | 10/1995 | Krupin . |
| 5,476,445 | 12/1995 | Baerveldt et al. . |
| 5,501,232 | 3/1996 | Ritleng . |
| 5,520,631 | 5/1996 | Nordquist et al. . |
| 5,558,629 | 9/1996 | Baerveldt et al. . |
| 5,558,630 | 9/1996 | Fisher . |
| 5,573,544 | 11/1996 | Simon et al. . |
| 5,584,152 | 12/1996 | Baerveldt . |
| 5,601,094 | 2/1997 | Reiss . |
| 5,722,948 * | 3/1998 | Gross ........................................ 604/8 |
| 5,785,674 * | 7/1998 | Mateen ...................................... 604/9 |
| 5,868,697 * | 2/1999 | Richter et al. ........................... 604/8 |

* cited by examiner

Primary Examiner—Angela D. Sykes  
Assistant Examiner—Pat Bianco  
(74) Attorney, Agent, or Firm—John J. Connors; Connors & Assoc.

(57) ABSTRACT

A medical device includes a valve comprising a pair of plates holding in tension a membrane folded over to form a chamber with an elongated, slit-like opening along adjoining edges. An inlet tube in communication with the chamber extends outwardly. The valve is installed in a pocket of a flexible distribution plate having ridges emanating from the pocket in a radial pattern. The device is implanted in the globe of the eye of a patient between the rectus muscles.

31 Claims, 6 Drawing Sheets

POCKET MEDICAL VALVE & METHOD

This application is a continuation-in-part of U.S. patent application Ser. No. 08/771,446, filed Dec. 20, 1996, entitled Device and Method For Treating Glaucoma, now U.S. Pat. No. 5,785,674, which is incorporated herein by reference and made a part of this application.

BACKGROUND OF THE INVENTION

1. Field of the Invention

This invention relates to medical devices which are implanted in the human eye, particularly to a valve which is easy to manufacture, performs reliably, is easy to surgically implant in the eye, and will remain functional for the life of the patient in which it is implanted. The valve of this invention has a unique shape and flexibility that improves performance and reduces the possibility of irritation when implanted on the eye of a glaucoma patient.

2. Background Discussion

Medical valves are used in a wide variety of applications within the human body. One such application is to treat glaucoma in patients where pharmacological treatment is not desirable. In this application, a valve is used to allow aqueous humor to flow in a controlled manner from the intraocular chamber of the eye to relieve excess pressure.

Several devices have been developed for relieving intraocular pressure. Thomas C. White in U.S. Pat. No. 4,554,918 has suggested one type of glaucoma valve where the aqueous humor flows from the intraocular chamber through a tube into an external reservoir. The end of the tube in communication with the reservoir has a very small opening that restricts the flow of aqueous humor into the reservoir. The reservoir, once filled, must be pressed periodically by the patient to force the contents through another tube into the body of the patient, where it is absorbed.

Another device used to treat glaucoma is discussed by Anthony C. B. Molteno in U.S. Pat. No. 4,457,757. This device includes a rigid plate having a tube in communication with the intraocular chamber. The aqueous humor flows from the intraocular chamber onto the surface of the plate and is absorbed by the body. The Molteno device does not have any pressure controlling mechanism, relying solely on the absorption rate of the bleb formed around the plate to maintain proper intraocular pressure.

A third device, suggested by George Baerveldt et al. in U.S. Pat. No. 5,476,445, is similar to the Molteno device except that Baerveldt uses a flexible plate which is often tucked under the muscles. The larger surface area is assumed to help reduce intraocular pressure over longer periods. But like Molteno, Baerveldt does not address the problem of hypotony. Since Baerveldt does not have a valve system, the doctors have to rely on other mechanisms to control the immediate outflow of aqueous humor causing hypotony.

These devices have been used to treat surgically glaucoma patients, but they do have disadvantages. The White valve suffers from the disadvantage that the patient must manually press the reservoir in order to force aqueous humor collected in the reservoir to escape and be absorbed by the body. Moreover, although the White valve is designed to maintain a proper amount of intraocular pressure, the valve's structure is not reliable because it depends upon a tiny opening in the end of the tube, which can easily become clogged with particulates. Nor is the White valve sensitive to minute pressure changes, since it merely limits flow rather than opening and closing at predetermined pressures.

The Molteno plate overcomes the objections of a manually actuated reservoir. However, it does not employ a valve to control pressure loss in the intraocular chamber, which creates the risk of hypotony. The Baerveldt device improves upon the Molteno plate, but does not mitigate the possibility of hypotony because it too does not utilize a pressure controlling mechanism to maintain intraocular pressure at an appropriate level. The flexibility of the Baerveldt device eases installation, but also creates the possibility that the flexible plate may collapse during installation, significantly reducing the absorption area available.

A valve invented by the Applicant and disclosed in U.S. Pat. No. 5,071,408 (herein referred to as the Glaucoma Valve) has many features that distinguish it from White, Molteno, and Baerveldt. This Glaucoma Valve uses a membrane under tension to form a trapezoidal chamber having an elongated, slit-like opening therein. The membrane responds to the slightest changes in pressure to expand or contract to open or close the opening. When opened, it provides a wide open mouth with parted lips that allows for free flow of fluid through it without any substantial resistance to fluid flow. This feature also substantially reduces the likelihood that the opening will be clogged by particulates. The trapezoidal configuration of the chamber renders the valve highly responsive to slight changes in pressure. In this application, the valve maintains a pressure of 10.0 millimeters (mm) of mercury (Hg), with an increase of 0.5 mm of Hg opening the valve. As soon as intraocular pressure reaches 10.0 mm of Hg, the valve is totally shut off to prevent further flow of aqueous humor from draining from the intraocular chamber. Thus, the Glaucoma valve utilized in this invention solves both the problem of over pressurization of the intraocular chamber due to blockage, and the problem of excessive loss of aqueous humor leading to hypotony. Two plates hold between them in tension the overlying membrane members which form between them the chamber. The slit-like opening is along adjoining, overlapping edges of the membrane members. Preferably, the membrane members are simply two halves of a thin sheet of elastic material having an hour-glass shape which is folded over upon itself. The two plates each include interlocking members that, upon the plates being pressed together, engage to place the membrane members disposed between the plates in tension.

SUMMARY OF THE INVENTION

The present invention is a medical device which is implanted in the eye of a patient. The device has a uniquely designed fluid distribution plate enhancing its ability to treat glaucoma.

This invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include the ability to maintain appropriate back-pressure, to induce the formation of a multi-chamber bleb, and ease of manufacture and implanting in a patient's eye.

The first feature of the medical device of this invention for treating a patient suffering from glaucoma is that it employs a modified Glaucoma Valve. The modified Glaucoma Valve is a one way valve in communication with the intraocular chamber of the eye which opens to allow fluid to drain from the chamber in response to pressure in the intraocular chamber exceeding a predetermined level. The valve comprises an elastic membrane in tension forming a slit-like opening which is normally closed and which opens when the pressure of the intraocular chamber exceeds the predetermined level. The membrane preferably comprises a sheet of siliconized rubber folded to form the slit-like opening, with the folded sheet being held in position in tension between a pair of rigid plates. The valve includes an inlet tube which is adapted to be inserted into the intraocular chamber of the patient.

The second feature is a distribution plate which is made from an enlarged sheet of flexible and resilient material such as, for example, siliconized rubber. This distribution plate has a pocket in which the valve is seated. The pocket, preferably C-shaped, is formed from the sheet which has one end folded upon itself to form the pocket. The valve may be positioned on the unfolded sheet and then the sheet folded around the valve to form the pocket, or the pocket may first be formed prior to inserting the valve into an open mouth in the pocket. Flexibility and resiliency of the material permits insertion of the valve into the pocket which stretches and then contracts to retain the valve once inserted in the pocket, simplifying manufacture. The pocket has opposite its open mouth a small opening therein. When the valve is inserted into the pocket, the inlet tube is guided into and through this small opening so that it extends through this opening, allowing it to be inserted into the intraocular chamber of the patient. The pocket is at one end of the distribution plate and the opposite end of the distribution plate has an indentation therein to permit this plate to be positioned next to but not touching the optic nerve of the eye when the medical device is attached to the globe of the eye of the patient. The valve is positioned in the pocket so that fluid exiting the slit-like opening flows out of the open mouth of the pocket onto the distribution plate. The distribution plate, excluding the pocket, preferably has an area of from 100 to 300 square millimeters. Optionally, the distribution plate may have markings thereon providing a guide for cutting the plate along these markings to reduce the area of the plate. Preferably, these cut lines are molded in cut-lines in the distribution plate thereby permitting the doctor to cut the plate to an appropriate size, determined by the physician's evaluation of the patient's fluid absorption requirements, eye ball size, and selection of device installation either under or between the rectus muscles.

The third feature is that the distribution plate has a plurality of ridges thereon. Preferably, these ridges have a series of openings thereon, and they are arranged in a radial manner originating at the pocket. The holes are at the top of the ridges and they extend through the distribution plate. This construction has several advantages. First, the ridges maintain structural integrity while allowing the plate itself to be thinner. A thinner plate increases the flexibility of thy Plate, thus ensuring close conformance to the spherical shape of the eyeball onto which the valve is installed. Second, the radial ridges provide stiffness in the direction of insertion of the plate, mitigating the possibility of buckling during installation. This reduces the possibility of the distribution plate collapsing when inserted into a scleral flap made by the surgeon during installation without reducing the plate's ability to conform closely to the surface of the globe of the eye. The radial pattern of the ridges encourages even distribution of aqueous humor emitted from the valve onto the entirety of the distribution plate. The holes along the ridges enable the tissue around the valve to grow through the plate, encouraging the creation of individual blebs between each pair of ridges, increasing the absorption area created by the distribution plate. The holes also provide a means for allowing the aqueous humor to flow to the bottom or underside of the plate, further increasing distribution area. The ridges create a convex surface onto which fluid flowing from the slit-like opening is received. The side of the plate opposite the ridges is a smooth concave surface so that it conforms generally to the surface of the globe of the eye. Thus, the medical device of this invention may be easily attached to the eye of the patient. The medical device is inserted within a scleral flap cut in the eye ball of the patient, with the smooth concave surface facing the interior of the eyeball. It is positioned between a major rectus muscle and a minor rectus muscle of the eye ball and the pocket end of the device is pointed towards the cornea of the eye ball. Due to the ridges with openings therein, the multiple blebs are formed over the flexible distribution plate, allowing for fluid from the interocular chamber to be quickly absorbed by the patient's body. The holes provide a path for tissue growth through the distribution plate, which encourages the formation of the multiple blebs.

This invention also includes a method for treating glaucoma by draining the intraocular chamber of the eye of a patient using the device of this invention. This method includes the following steps:

(a) providing a medical device including
a one way valve comprising an elastic membrane in tension forming a pressure chamber with a slit-like opening therein and an inlet tube with one end in communication with said pressure chamber and another end adapted to be placed in communication with the intraocular chamber of the eye, said slit-like opening being normally closed and opening when the pressure of the intraocular chamber exceeds a predetermined level, and
a distribution plate made of a flexible material and having a ridged convex surface onto which fluid flowing from the slit-like opening is received and a smooth concave surface so that said concave surface may be placed on the eye of the patient, and said distribution plate having a pocket in which said valve is seated, said docket having an opening therein with the inlet tube extending through said opening so that said tube may be inserted into the intraocular chamber, (b) positioning the medical device within a scleral flap on an eye ball of the patient, with the smooth concave surface facing the interior of the eyeball between a major rectus muscle and a minor rectus muscle of the eye ball and the pocket end of the device pointed towards the cornea of the eye ball, c) inserting one end of the inlet tube into the intraocular chamber of the eye ball to enable fluid to drain through the slit-like opening onto the flexible distribution plate, with multiple blebs forming over said flexible distribution plate, allowing for this fluid to be quickly absorbed by the patient's body, and (d) attaching the medical device to the eyeball.

BRIEF DESCRIPTION OF THE DRAWING

The preferred embodiments of this invention, illustrating all its features, will now be discussed in detail. These embodiments depict the novel and non-obvious medical device and method of this invention as shown in the accompanying drawing, which is for illustrative purposes only. This drawing includes the following figures (FIGS.), with like numerals indicating like parts:

FIG. 6b is a cross-sectional view of the flexible distribution plate taken along line 6b—6b of FIG. 6a;

FIG. 7b is a cross-sectional view taken along line 7b—7b of FIG. 7a;

DESCRIPTION OF THE PREFERRED EMBODIMENTS

Figure 1:
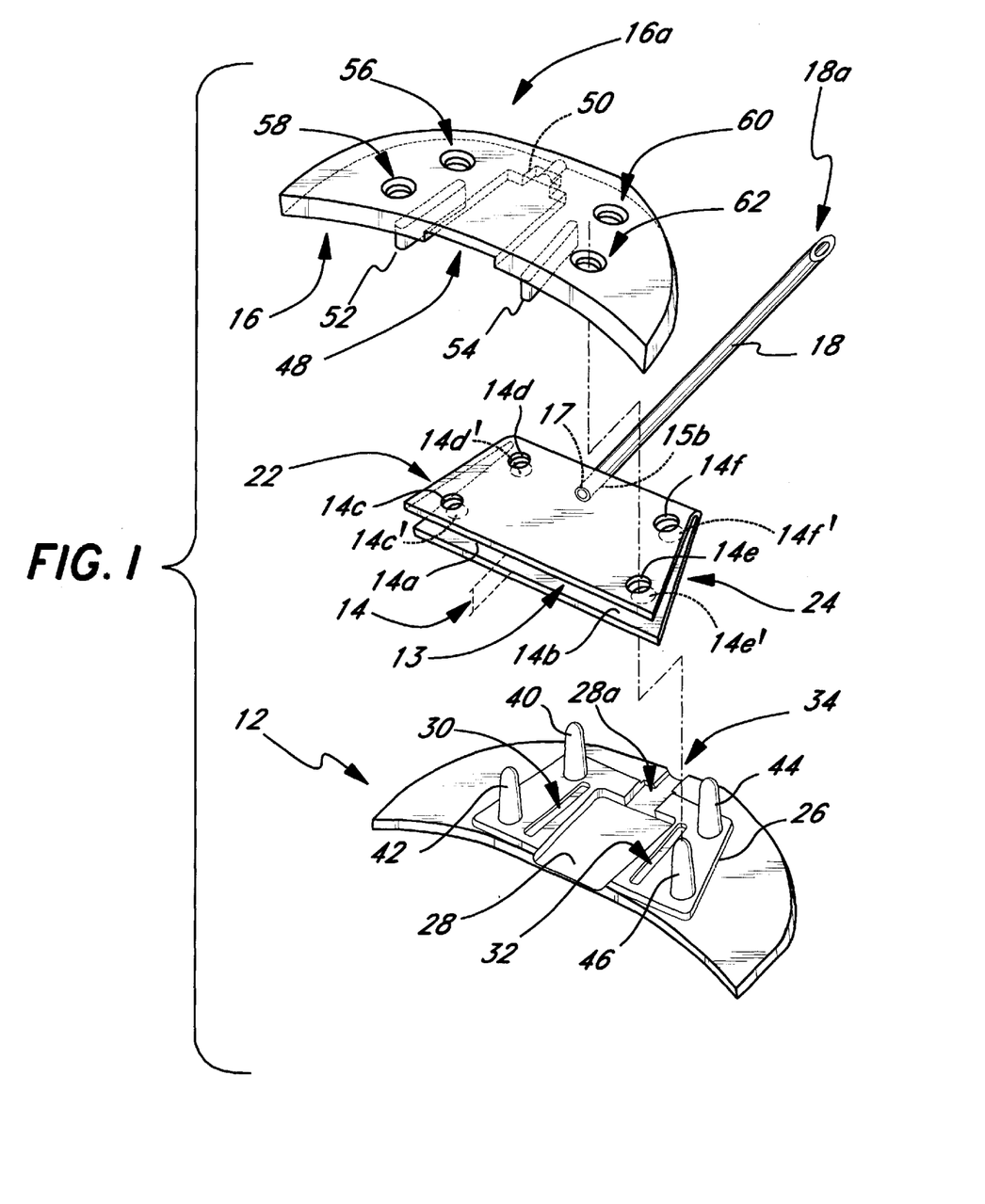
FIG. 1 is an exploded perspective view of the valve used in this invention.

As depicted in FIG. 1, the valve 10 used in the medical device 8 of this invention includes a bottom plate 12, a flexible, silicoized rubber membrane 14, a top plate 16, and a siliconized rubber inlet tube 18. The membrane 14 is folded to form a pair of essentially identically trapezoidal shaped membrane members 14a and 14b. The membrane members 14a and 14b are placed between aligned and spaced apart top plate 16 and bottom plate 12 as illustrated in FIG. 2b and these plates are pressed together and interlocked to hold the folded membrane 14 in position.

Figure 8:
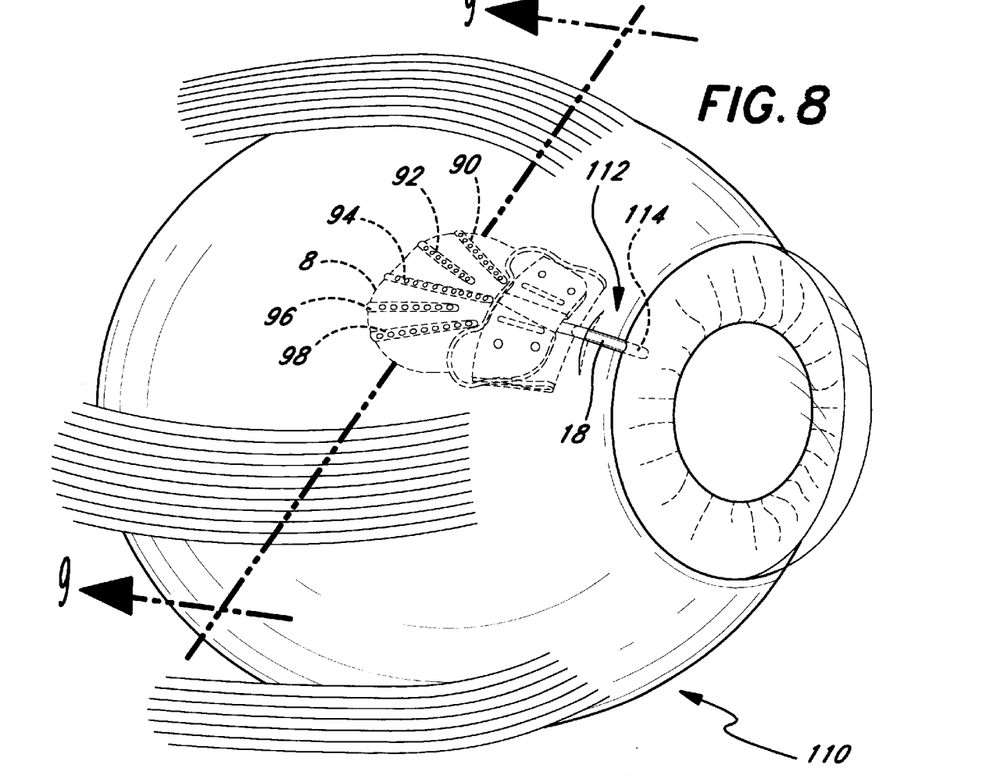
FIG. 8 is a perspective view of showing the medical device of this invention installed in the eye ball of a patient.

The membrane 14 is originally in a non-folded condition, and it has an hourglass-like shape narrowing at the central section 15a and then expanding outwardly therefrom in both directions. The membrane 14 has a thickness ranging between 0.004 and 0.007 inch, preferably between 0.005 and 0.006 inch. There is a central opening 15b in the member 14 and two sets of four spaced apart openings 14c, 14c', 14d, 14d', 14e, 14e', 14f, and 14f' along its opposed irregular sides 22 and 24. These holes 14c through 14f and 14c' through 14f' have a diameter of approximately 0.02 inch. A suitable siliconized rubber for use as the membrane 14 and the inlet tube 18. One end of the inlet tube 18 is inserted central opening 15b. The inlet tube 18 extends from the membrane 14 so that a free end 18a may be surgically inserted into the intraocular chamber 20 of the eye as illustrated in FIG. 8.

The bottom plate 12 has a generally crescent-shaped configuration, with a raised four-sided central area 26, which includes therein a centrally located depression 28 of a generally trapezoidal configuration. On each side of this depression, running along substantially its entire length, are two grooves 30 and 32. At the one end 28a of the depression 28 is an indentation 34 which receives the tube 18. On the outside of each of the two grooves 30 and 32 are a pair of raised pins 40 and 42, and 44 and 46, respectively.

The top plate 16 is also a generally crescent-shaped member having a centrally located generally trapezoidal shaped depression 48 on the plate's 16 bottom surface with an indentation 50 along its one side 16a. There are a pair of elongated finger elements 52 and 54 extending downwardly which interlock, respectively, in the grooves 30 and 32 in the bottom plate 12 when the two plates are pressed together. There are pairs of bores with countersinks 56 and 58, and 60 and 62, respectively, on the outside of each pair of finger elements 52 and 54, which receive the pairs of pins 40 and 42, and 44 and 46 in the bottom plate 12 when the top plate 16 and bottom plate are aligned and pressed together.

Both the top and bottom plates 12 and 16 have segmented spherical shape so that they conform to the curvature of the eyeball. Both plates 12 and 16 are made of a material that will not be rejected by the body. Suitable materials from which to make plates 12 and 16 are siliconized rubber, polypropylene, and polymethyl-methylacrelate (PMMA).

Figure 2A:
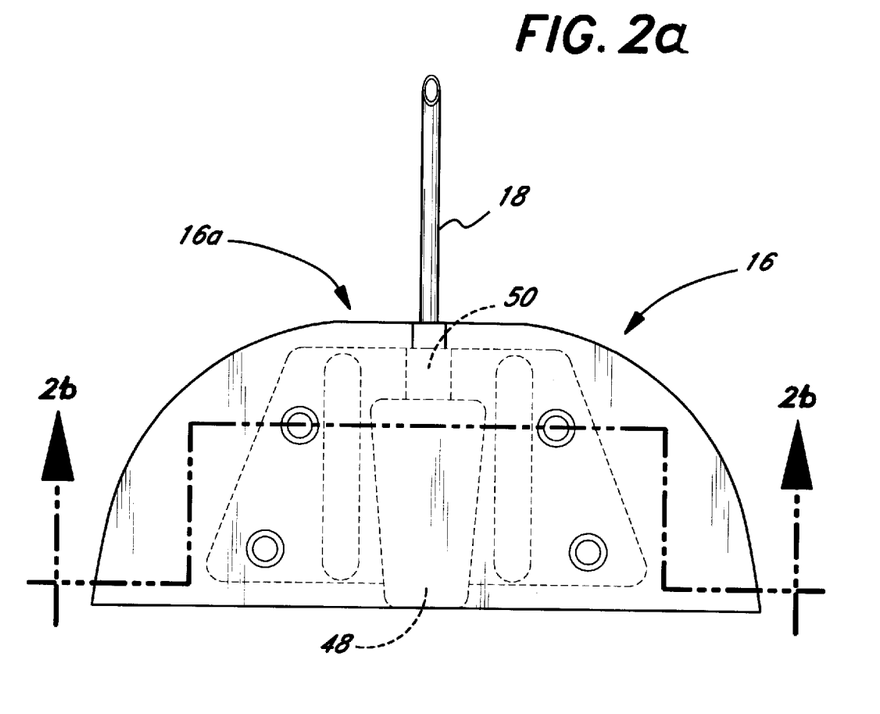
FIG. 2a is a plan view of the top of the valve.
Figure 2B:
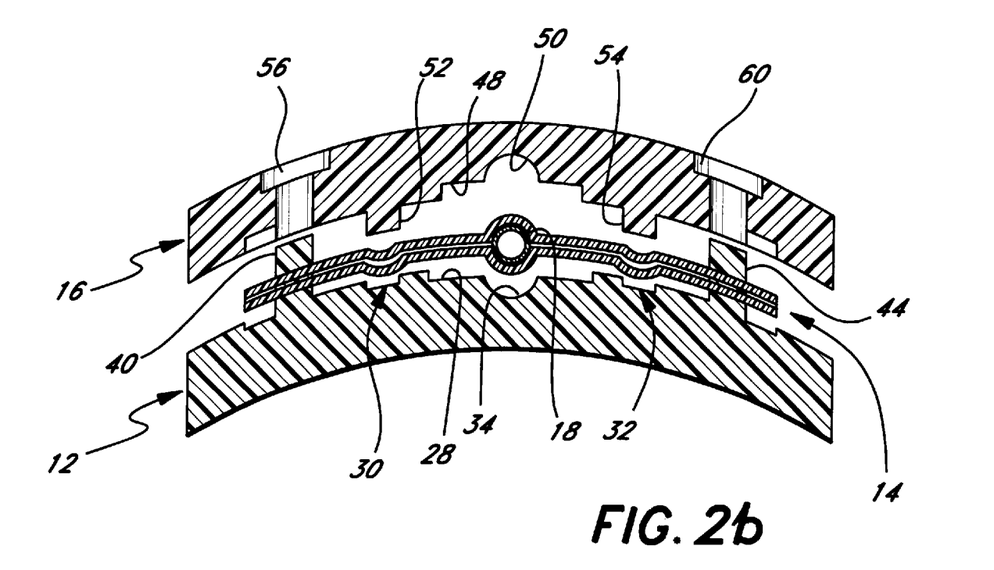
FIG. 2b is a cross-sectional view taken along line 2b—2b of FIG. 2a showing the two plates positioned to be pressed together to hold the folded membrane therebetween.

FIG. 2a and FIG. 2b show the method of assembling the valve 10. The inlet tube 18 is inserted into the central opening 15b and bonded to membrane 14. With the membrane 14 folded inwardly upon itself, it is placed between top plate 16 and bottom plate 12 and these plates are interconnected together, with the tube's outwardly extending section being placed between the indentations 34 and 50, respectively, in the plates 12 and 16. An adhesive 17 is used to bond the tube 18 and the membrane 14. An example of a suitable adhesive is medical grade Silastic A, made by Dow Corning Corporation.

As depicted in FIG. 1, the overlapping membrane members 14a and 14b are held in position by pins 40, 42, 44, and 46 of bottom plate 12, which extend through openings 14c and 14c', 14d and 14d', 14e and 14e', and 14f and 14f' in the membrane and into bores 56, 58, 60, and 62 in the top plate 16 when the bottom plate 12 and top plate 16 are pressed together. This action also causes finger elements 52 and 54 extending from the bottom of top plate 16 to be wedged into grooves 30 and 32 of bottom plate 12. This causes the membrane 14 to stretch, placing it in tension so that a slit-like opening 13 is formed between the edges of the overlapping membrane members 14a and 14b. The trapezoidal depressions 28 and 48, respectively, in the bottom plate 12 and top plate 16, create a trapezoidal-shaped chamber (not shown) between the overlapping membrane members 14a and 14a. Fluid from the eye flows through the tube 18 and exits the tube 18 and flows into this trapezoidal-shaped chamber.

Figures 3A, 3B, 4:
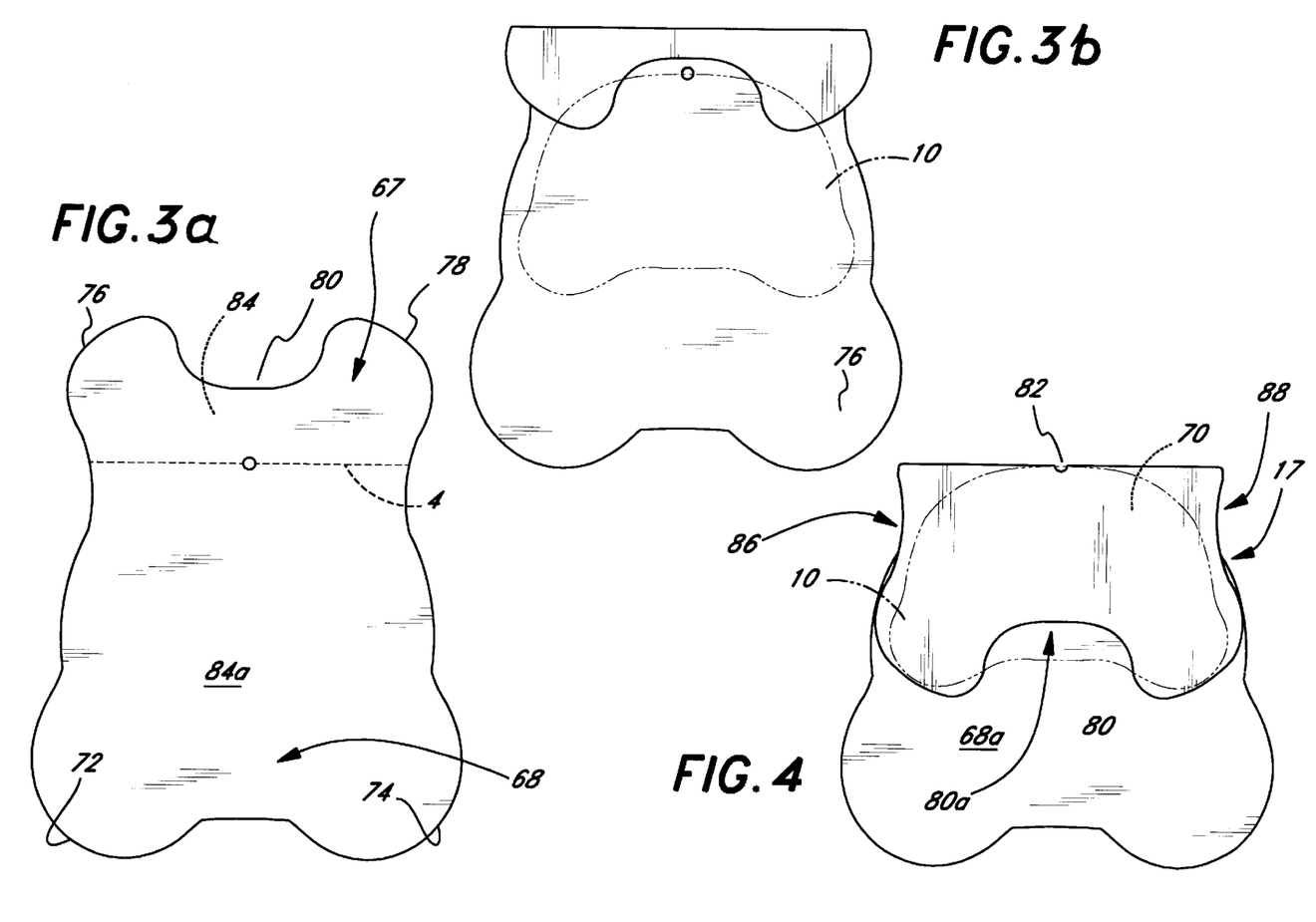
FIG. 3a is a plan view of a flexible sheet used to form the C-shaped pocket for the valve body member and the fluid distribution plate.
FIG. 3b is a plan view of the flexible sheet being folded to form the generally C-shaped pocket for the medical device of this invention.
FIG. 4 is a plan view of the folded sheet which forms the flexible fluid distribution plate and the C-shaped pocket into which the valve is placed.

FIG. 3a depicts the general shape of a flexible sheet 67 of siliconized rubber which is folded to form a C-shaped pocket 70 (FIG. 6a) adjacent a distribution plate 68. The thickness of the sheet typically ranges between about 0.005 and 0.05 inch and has an area of about 5200 square millimeters. There are two versions of the distribution plate 68: a version without ridges (FIGS. 3a through 5) and a version with ridges (FIGS. 6a through 9). The purpose of the ridges will be discussed subsequently in detail. The flexible sheet 67 has a wider lower section having a pair of lobes 72 and 74 and an upper narrower section having a pair of smaller lobes 76 and 78. There is a central cutout 80 formed therebetween the lobes 76 and 78, and a bore 82 located below the central cutout 80 provides an entry point for the tube 18 extending from the valve 10.

Figure 5:
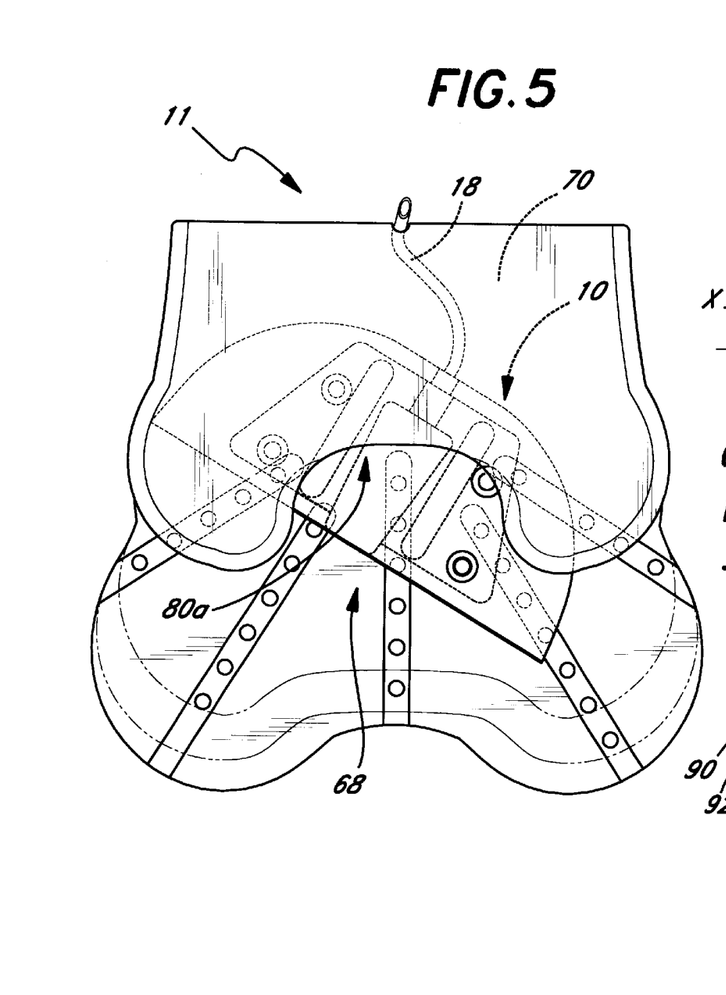
FIG. 5 is a plan view of the valve partially inserted into the C-shaped pocket.

FIG. 3b and FIG. 4 show the formation of the C-shaped pocket 70 by folding an upper flap 84 of the sheet 67 along a line 4—4, FIG. 3a. This folded upper flap 84 is bonded with an adhesive 17 to the surface 84a of the lower portion of the sheet 67 along marginal adhesion areas 86 and 88, forming the generally C-shaped pocket 70. After folding, the cutout 80 overlies the surface 84a, but it is not bonded to the surface 84a, so that a central open mouth 80a is formed that allows the valve 10 to be inserted into the pocket 10 as illustrated in FIG. 5. The bore 82 is opposite the open mouth 80 after folding. The open mouth 80a of the pocket 70 faces the distribution plate 68, so that fluid escaping from the valve 10 is collected on the surface 68a of the plate 68. The area of this surface 68a typically ranges between about 100 and 300 square millimeters, and preferably is approximately 250 square millimeters.

As shown in FIG. 5, the valve 10 may inserted into C-shaped pocket 70 by guiding the tube 18 first through bore 82, then inserting the valve 10 at an angle through the open mouth 80a into the pocket 70. The flexibility and resiliency of the sheet material forming the pocket 70 permits the pocket to stretch sufficiently to allow insertion of valve 10. Once installed, the pocket 70 recovers its shape after insertion of the valve 10 to maintain the proper positional relationship of the valve 10 and distribution plate 68 without additional adhesives or fasteners. After insertion into the pocket 70, the valve 10 is oriented so that the longitudinal axis of the valve is generally at a right angle to the longitudinal axis of the distribution plate 68. Although, the pocket 70 may first be formed and the valve 10 inserted into it, the valve could be placed on the unfolded sheet 67 in the correct position and the upper upper flap 84 folded over the valve.

Figure 6A:
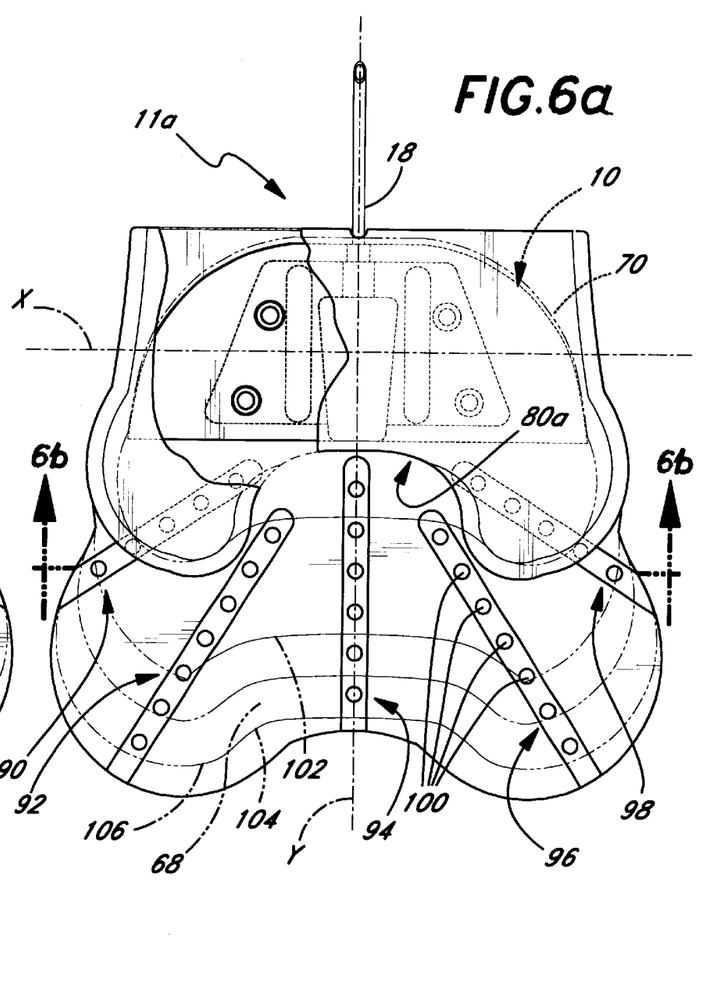
FIG. 6a is a plan view of the medical device of this invention showing the installed position of the valve within the C-shaped pocket.
Figure 6B:
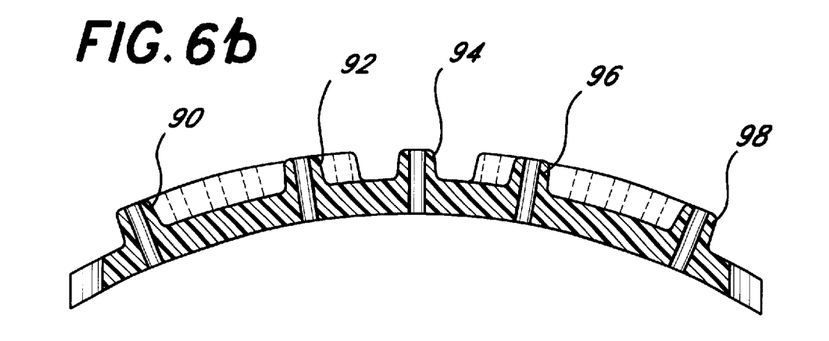
Figure 7A:
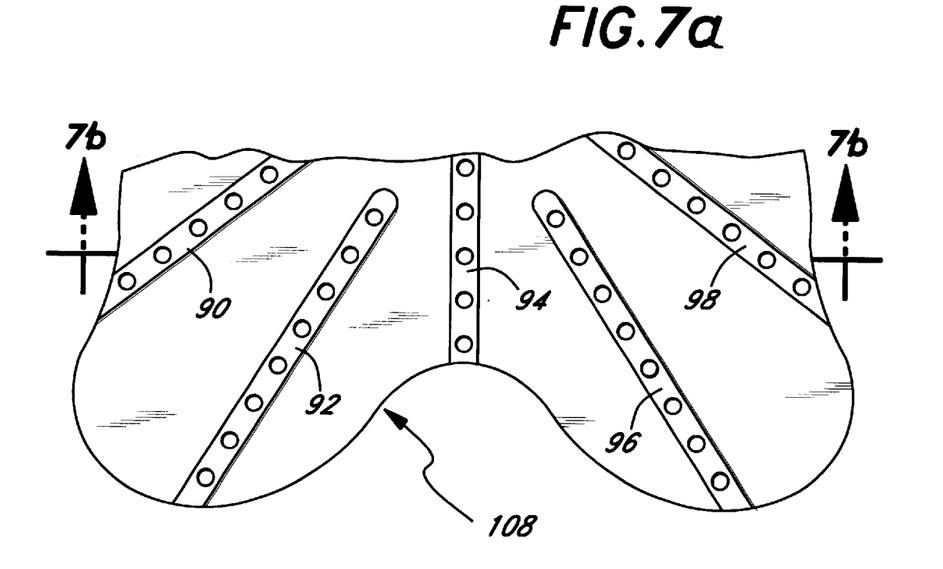
FIG. 7a is a plan view, of showing a portion of a flexible distribution plate cut away.
Figure 7B:
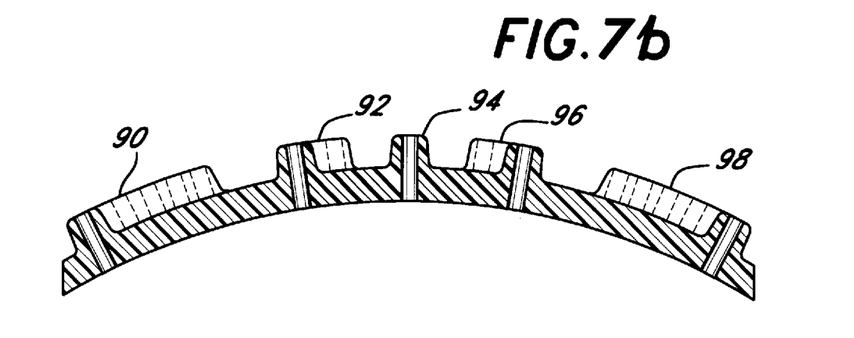

FIG. 6a shows an alternate embodiment of this invention where the distribution plate 68 includes five ridges 90, 92, 94, 96, and 98 disposed in a radial pattern extending from the central cutout 80 to the edge of the plate. The valve 10 is fully seated within the C-shaped pocket 70 in its proper orientation so that the longitudinal axis X of the valve is generally at a right angle to the longitudinal axis Y of the distribution plate 68, thereby allowing fluid escaping from the slit-like opening 13 to flow onto the surface 84a of the plate 68. The ridges 90, 92, 94, 96, and 98 have a plurality of 0.02 inch diameter bores 100 at intervals of 0.03 inches along the length of the ridges. As best seen in FIG. 6b, the ridges 90, 92, 94, 96, and 98 are approximately 0.04 inches thick and 0.04 inches wide, and the distribution plate 68 is nominally 0.02 inches thick. This pattern of ridges, in conjunction with the flexibility of the distribution plate 68 material, makes the medical device 8 much more conformable to the shape of the globe of the eye. Also, on the distribution plate 68 are molded in cut lines 102, 104, and 106, which provide cutting guides to allow a surgeon to reduce easily the surface area of the distribution plate 68 based on specific patient requirements. For example, FIG. 7a shows a distribution plate 68 with a cutout 108 to avoid contact with the optic nerve of the eye.

Figure 9:
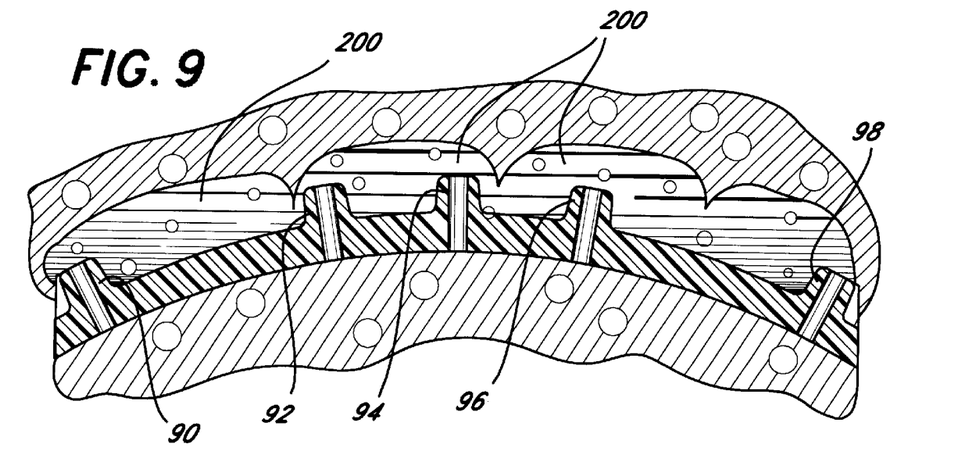
FIG. 9 is a cross-sectional view of the medical device taken along line 9—9 of FIG. 9, showing the formation of multiple blebs around the distribution plate.

As best illustrated in FIGS. 8 and 9, the medical device 8 of this invention may be installed on the eye ball 110 of a patient by first inserting inlet tube 18 into the intraocular chamber of the eye ball 110, then placing the medical device 8 beneath a sclera flap 112 which is cut from the exterior of the eye ball 110. The orientation of ridges 90, 92, 94, 96, and 98 enhance the rigidity of the distribution plate 68 in the direction of device 8 insertion under the scleral flap 112, ensuring that the plate 68 will not collapse during insertion. The medical device 8 is held in position by running sutures through pocket 70 as required to affix the device 8 to the eye ball 110.

In accordance with the method of this invention, the device 8 is placed between the major and minor rectus muscles as opposed to inserting the device underneath these muscles, as is the case with some ocular implant devices. The placement of the device as depicted in FIG. 8 is highly desirable, since it minimizes the problems associated with strabism, or eye squinting, which is frequently induced when ocular devices are positioned underneath the major and minor rectus muscles. With the device 8 implanted in the patient, as illustrated in FIG. 8, pressure within the intraocular chamber 114 forces the aqueous humor 124 through inlet tube 18 into the trapezoidal chamber. When the chamber is filled and the pressure in the intraocular chamber 114 exceeds 10 millimeters of mercury, the membrane members 14a and 14, spread apart, but only for such time period as this differential pressure exists. Once the differential pressure is below 10 millimeters of mercury, the membrane members 14a and 14b, being under tension, close off the slit-like opening 13 automatically so that aqueous humor 124 will no longer escape from the intraocular chamber 114, thereby avoiding hypotony.

Within a short period of time after the installation, blebs 200 form around the medical device 8. A bleb is tissue membrane that traps the aqueous humor 124 collecting on and under the distribution plate 68. This entrapped fluid is then slowly absorbed into the body of the patient. FIG. 9 illustrates the formation of multiple blebs around the medical device 8 after implantation. The ridges 92, 94, and 96 encourage the formation of multiple bleb chambers 116, 118, 120, and 122 because tissue is allowed to grow through the multiple bores 100. The bores 100 also provide a percolation path for the aqueous humor 124 to travel to the bottom of distribution plate 68. The formation of multiple blebs 116, 118, 120, and 122 between the ridges 92, 94, and 96, as well as below the distribution plate 68 significantly increases the tissue surface area available for absorption of aqueous humor 124, thereby increasing the device's 8 performance.

Scope of the Invention

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A medical device for treating a patient suffering from glaucoma and adapted to be attached to the globe of the eye of the patient, including a one way valve in communication with the intraocular chamber of the eye which opens to allow fluid to drain from said chamber in response to pressure in the intraocular chamber exceeding a predetermined level, said valve comprising an elastic membrane in tension forming a slit-like opening which is normally closed and which opens when the pressure of the intraocular chamber exceeds said predetermined level, said membrane comprising a sheet of siliconized rubber folded to form said slit-like opening, with said folded sheet being held in position tension between a pair of rigid plates, and a distribution plate made of a flexible material, said sheet material being folded to form said distribution plate with a pocket therein having an open mouth, said valve being seated in the pocket.

2. The medical device of claim 1 where the flexible material of the distribution plate is siliconized rubber.

3. The medical device of claim 1 where the sheet material has opposed ends and an intermediate surface portion between said opposed ends, with one end folded inward and overlying the intermediate surface portion to provide overlapping marginal areas that are bonded with an adhesive to form the pocket.

4. The medical device of claim 3 where the valve is positioned on the unfolded sheet and then the sheet is folded around the valve to form the pocket.

5. The medical device of claim 1 where the pocket is formed prior to seating the valve in the pocket.

6. The medical device of claim 1 where the pocket has an opening therein, said opening being formed in the sheet material prior to folding, and the valve includes an inlet tube that extends through said opening and is adapted to be inserted into the intraocular chamber.

7. The medical device of claim 1 where the distribution plate has a plurality of ridges thereon.

8. The medical device of claim 7 where the ridges have a series of openings thereon.

9. The medical device of claim 7 where the ridges are arranged in a radial manner originating at the pocket.

10. The medical device of claim 1 where the distribution plate, excluding the pocket, has an area of from 100 to 300 square millimeters.

11. The medical device of claim 1 where the distribution plate has markings thereon providing a guide for cutting the plate along said markings to reduce the area of said plate.

12. A medical device for treating a patient suffering from glaucoma and adapted to be attached to the globe of the eye of the patient, including a one way valve in communication with the intraocular chamber of the eye which opens to allow fluid to drain from said chamber in response to pressure in the intraocular chamber exceeding a predetermined level, and a distribution plate made of a flexible sheet material, said sheet material being folded to form said distribution plate with a pocket therein having an open mouth, said valve being seated in the pocket and the pocket being at one end of the distribution plate and the opposite end of the distribution plate having an indentation therein to permit said plate to be positioned next to but not touching the optic nerve of the eye when the medical device is attached to the globe of the eye of the patient.

13. A medical device for treating a patient suffering from glaucoma and adapted to be attached to the globe of the eye of the patient, including a one way valve comprising an elastic membrane in tension forming a pressure chamber with a slit-like opening therein where the membrane comprises a sheet of siliconized rubber folded to form said slit-like opening, and an inlet tube with one end in communication with said pressure chamber and another end adapted to be placed in communication with the intraocular chamber of the eye, said slit-like opening being normally closed and opening when the pressure of the intraocular chamber exceeds a predetermined level, and a distribution plate made of a flexible sheet material folded to form said distribution plate with a pocket therein having an open mouth and having a surface onto which fluid flowing from the slit-like opening is received, said surface having an area of from 100 to 300 square millimeters, and said valve being seated in said pocket.

14. The medical device of claim 13 where the flexible material of the distribution plate is siliconized rubber.

15. The medical device of claim 13 where the sheet material has opposed ends and an intermediate surface portion between said opposed ends, with one end folded inward and overlying the intermediate surface portion to provide overlapping marginal areas that are bonded with an adhesive to form the pocket.

16. The medical device of claim 5 where the valve is positioned on the unfolded sheet and then the sheet is folded around the valve to form the pocket.

17. The medical device of claim 13 where the pocket is formed prior to seating the valve in the pocket.

18. The medical device of claim 13 where the distribution plate has a plurality of ridges thereon.

19. The medical device of claim 18 where the ridges have a series of openings thereon.

20. The medical device of claim 18 where the ridges are arranged in a radial manner originating at the pocket.

21. A medical device for treating a patient suffering from glaucoma and adapted to be attached to the globe of the eye of the patient, including a one way valve comprising an elastic membrane in tension forming a pressure chamber with a slit-like opening therein and an inlet tube with one end in communication with said pressure chamber and another end adapted to be placed in communication with the intraocular chamber of the eye, said slit-like opening being normally closed and opening when the pressure of the intraocular chamber exceeds a predetermined level, and a distribution plate made of a flexible material and having a surface onto which fluid flowing from the slit-like opening is received, said surface having an area of from 100 to 300 square millimeters, and said distribution plate having a pocket in which said valve is seated, the pocket being at one end of the distribution plate and the opposite end of the distribution plate having an indentation therein to permit said plate to be positioned next to but not touching the optic nerve of the eye when the medical device is attached to the globe of the eye of the patient.

22. A medical device for treating a patient suffering from glaucoma and adapted to be attached to the globe of the eye of the patient, including a one way valve comprising an elastic membrane in tension forming a pressure chamber with a slit-like opening therein where the membrane comprises a sheet of siliconized rubber folded to form said slit-like opening, and an inlet tube with one end in communication with said pressure chamber and another end adapted to be placed in communication with the intraocular chamber of the eye, said slit-like opening being normally closed and opening when the pressure of the intraocular chamber exceeds a predetermined level, and a distribution plate made of a flexible sheet material and having a surface onto which fluid flowing from the slit-like opening is received, and said distribution plate having a pocket in which said valve is seated, said sheet material being folded to form said distribution plate with a pocket therein having an open mouth, said sheet material having opposed ends and an intermediate surface portion between said opposed ends, with one end folded inward and overlying the intermediate surface portion to provide overlapping marginal areas that are bonded with an adhesive to form the pocket, said pocket haveint an opening threin opposite said open mouth with the inlet tube extending thruogh said opening so theat said tube may be inserted into the intraocular chamber.

23. The medical device of claim 22 where the flexible material of the distribution plate is siliconized rubber.

24. The medical device of claim 22 where the valve is positioned on the unfolded sheet and then the sheet is folded around the valve to form the pocket.

25. The medical device of claim 22 where the pocket is formed prior to seating the valve in the pocket.

26. The medical device of claim 22 where the distribution plate, excluding the pocket, has an area of from 0.002 and 0.004 square inches.

27. The medical device of claim 22 where the distribution plate has markings thereon providing a guide for cutting the plate along said markings to reduce the area of said plate.

28. The medical device of claim 22 where the distribution plate has a plurality of ridges thereon.

29. The medical device of claim 28 where the ridges have a series of openings thereon.

30. The medical device of claim 28 where the ridges are arranged in a radial manner originating at the pocket.

31. A medical device for treating a patient suffering from glaucoma and adapted to be attached to the globe of the eye of the patient, including a one way valve comprising an elastic membrane in tension forming a pressure chamber with a slit-like opening therein and an inlet tube with one end in communication with said pressure chamber and another end adapted to be placed in communication with the intraocular chamber of the eye, said slit-like opening being normally closed and opening when the pressure of the intraocular chamber exceeds a predetermined level, and a distribution plate made of a flexible material and having a surface onto which fluid flowing from the slit-like opening is received, and said distribution plate having a pocket in which said valve is seated, said pocket having an opening therein with the inlet tube extending through said opening so that said tube may be inserted into the intraocular chamber, the pocket being at one end of the distribution plate and the opposite end of the distribution plate having an indentation therein to permit said plate to be positioned next to but not touching the optic nerve of the eye when the medical device is attached to the globe of the eye of the patient.

* * * * *

UNITED STATES PATENT AND TRADEMARK OFFICE
CERTIFICATE OF CORRECTION

PATENT NO. : 6,261,256 B1
DATED : July 17, 2001
INVENTOR(S) : Abdul Mateen Ahmed It is certified that error appears in the above-identified patent and that said Letters Patent is hereby corrected as shown below:

Column 5,
Line 40, "silicoized" should be spelled -- siliconized --.

Column 6,
Line 50, change second "14a" to "14b" to read -- 14a and 14b --

Column 7,
Line 30, remove the second word "upper"

Column 9,
Line 1, insert -- in -- between "position and tension" to read -- position in tension --
Line 3, insert -- sheet -- before "material"

Column 10,
Line 15, change "claim 5" to -- claim 15 --

Column 11,
Line 8, "haveint" should be -- having --
Line 8, "threin" should be -- therein --
Line 10, "theat" should be -- that --

Signed and Sealed this

Thirteenth Day of July, 2004

JON W. DUDAS
*Acting Director of the United States Patent and Trademark Office*